United States Patent [19]

Olson

[11] 4,216,069
[45] Aug. 5, 1980

[54] DETECTOR FOR TRACE LEAD IN GASOLINES

[75] Inventor: Don C. Olson, Houston, Tex.

[73] Assignee: Shell Oil Company, Houston, Tex.

[21] Appl. No.: 8,016

[22] Filed: Jan. 31, 1979

Related U.S. Application Data

[62] Division of Ser. No. 908,292, May 22, 1978, Pat. No. 4,153,517.

[51] Int. Cl.² .............................................. G01N 27/46
[52] U.S. Cl. ................................. 204/195 R; 324/425; 422/64
[58] Field of Search ............ 204/1 T, 195 R; 422/64; 324/29

[56] References Cited

U.S. PATENT DOCUMENTS

| | | | |
|---|---|---|---|
| 2,768,879 | 10/1956 | Hewson | 422/64 |
| 2,879,141 | 3/1959 | Skeggs | 422/64 |
| 3,499,733 | 3/1970 | Abbott et al. | 422/64 |
| 3,960,690 | 6/1976 | Olson | 204/195 R |

Primary Examiner—G. L. Kaplan

[57] ABSTRACT

An improved galvanic detector for measuring trace amounts of tetralkyl lead in gasoline having a sample holder mounted in a turntable. A disc of dried porous material is placed in the holder and a small sample of gasoline placed on the porous material and allowed to evaporate for a pre-set time to flash off the olefins. The turntable is then rotated to pass the disc over the sensing electrode of the galvanic cell and the peak value of current signal produced by the galvanic cell is measured and recorded.

5 Claims, 4 Drawing Figures

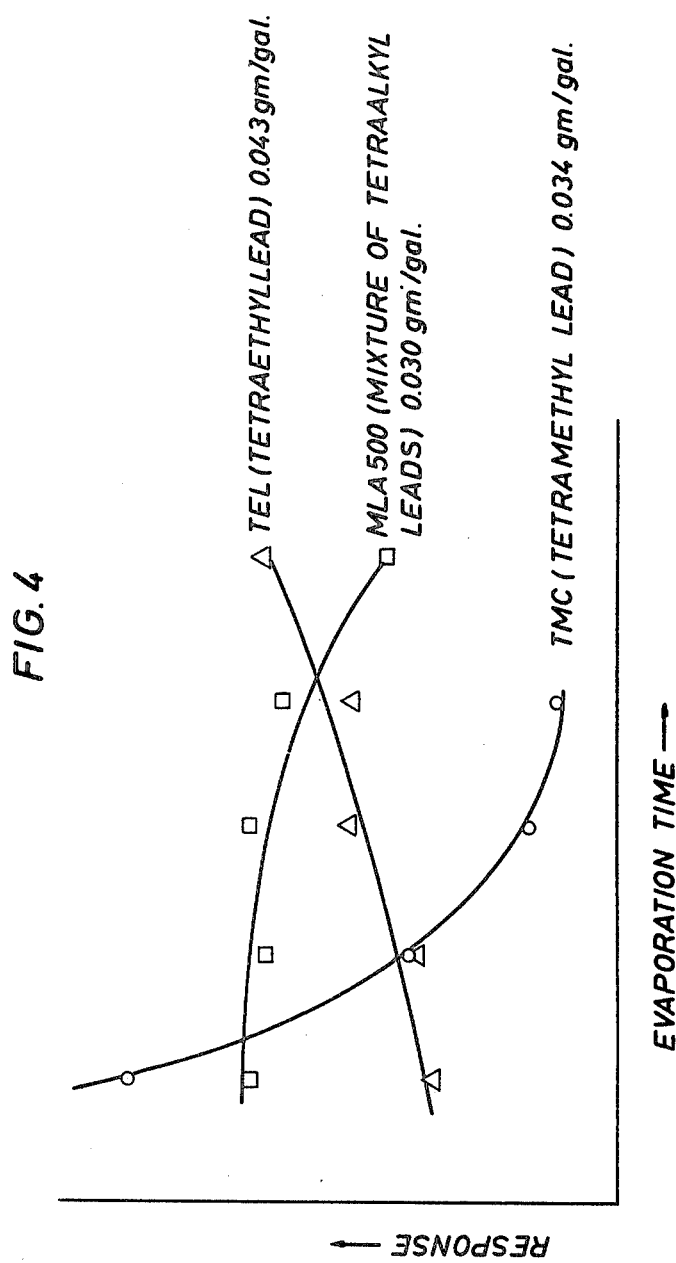

DETECTOR FOR TRACE LEAD IN GASOLINES

This is a division of application Ser. No. 908,292, filed May 22, 1978 and now U.S. Pat. No. 4,153,517.

BACKGROUND OF INVENTION

The present invention is an improved version of the method and apparatus for measuring trace amounts of tetraalkylleads in gasoline described in U.S. Pat. No. 3,960,690. This patent describes a method and apparatus in which a small sample of gasoline is injected into a system. A carrier gas is used to transport the sample to a vaporizer and filter for removing aromatics and olefins. The sample of gasoline is discharged from the filter to an electrochemical cell of the type known as galvanic sensor whose output signal is integrated or otherwise utilized to obtain a measurement of the quantity of the lead alkyl in the gasoline sample.

From the above brief description, it is seen that the method and apparatus of the above patent requires the use of a carrier gas to transport the gasoline sample through the vaporizing furnace and filter. In addition, the filter comprises a packed column, for example, a column packed with conventional chromatographic partitioning materials which will absorb the aromatics and olefins in the sample. Thus, the system requires a supply of carrier gas and a packed column which must be periodically renewed. In addition, the method requires some means for heating the vaporizing furnace to vaporize the sample.

BRIEF DESCRIPTION OF THE INVENTION

The present invention solves the above problems by providing a simplified method and apparatus utilizing the galvanic cell of the above patent to measure trace amounts of lead alkyls in gasoline. In particular, the invention utilizes an apparatus which has provisions for mounting a porous sample carrier on which a sample of the gasoline could be replaced. The porous sample carrier is then exposed to air for a pre-determined time to permit the aromatics and olefins to evaporate from the sample. After the elapse of the pre-determined time, the porous sample carrier is moved so that it passes over the sensing electrode of the galvanic cell. This permits a small amount of the lead alkyl to contact the sensing electrode by evaporation and transport across a thin air gap between the sample carrier and the sensing electrode. The small amount of tetraalkyllead contacting the galvanic cell will produce an output pulse. The amplitude of the output pulse can be correlated directly with the amount of tetraalkyllead in the gasoline sample.

The length of time which the porous medium is exposed to air to evaporate the aromatics and olefins from the gasoline sample can vary with the particular type of tetraalkyllead. In the case of tetramethyl lead (TML) or a mixture of tetraalkyllead compounds (MLA 500) relatively short operation times are desired, for example, one to two minutes; while in the case of tetraethyl lead (TEL) slightly longer evaporation times are desirable, for example, four to five minutes.

The apparatus used in the present invention may be relatively simple and comprises a turntable which is driven by a suitable motor means. The turntable is provided with a recess or sample receiving holder in which a disc of porous material, for example, dry filter paper, may be placed. The galvanic cell is mounted so that as the turntable rotates the recess or sample holding means will pass directly over the sensing electrode of the cell. In actual practice, it is preferable to have two sample holding means located diametrically opposite each other on the turntable so that when one sample has passed over the galvanic cell a second sample may be placed in the opposite sample-holding means. This will permit rapid measurement of the lead levels in a large number of gasoline samples. A result can be obtained by using a single sample holder and rotating it in opposite directions for alternate samples.

BRIEF DESCRIPTION OF THE DRAWINGS

The present invention will be more easily understood from the following detailed description of the preferred embodiment when taken in conjunction with the attached drawings in which:

FIG. 4 is a plot of the evaporation time versus lead levels for various lead alkyls.

PREFERRED EMBODIMENTS

Figure 1:
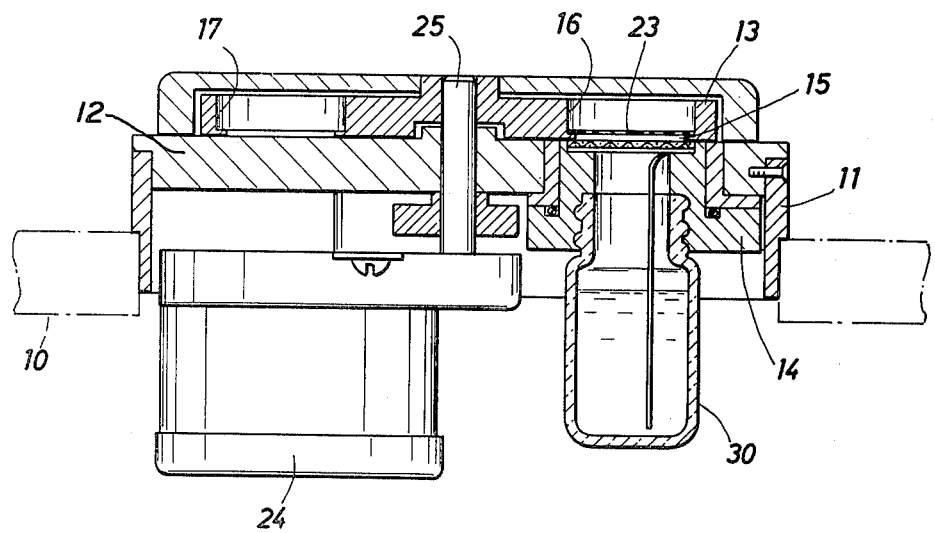
FIG. 1 is an elevation view of the apparatus used in the present invention.
Figure 2:
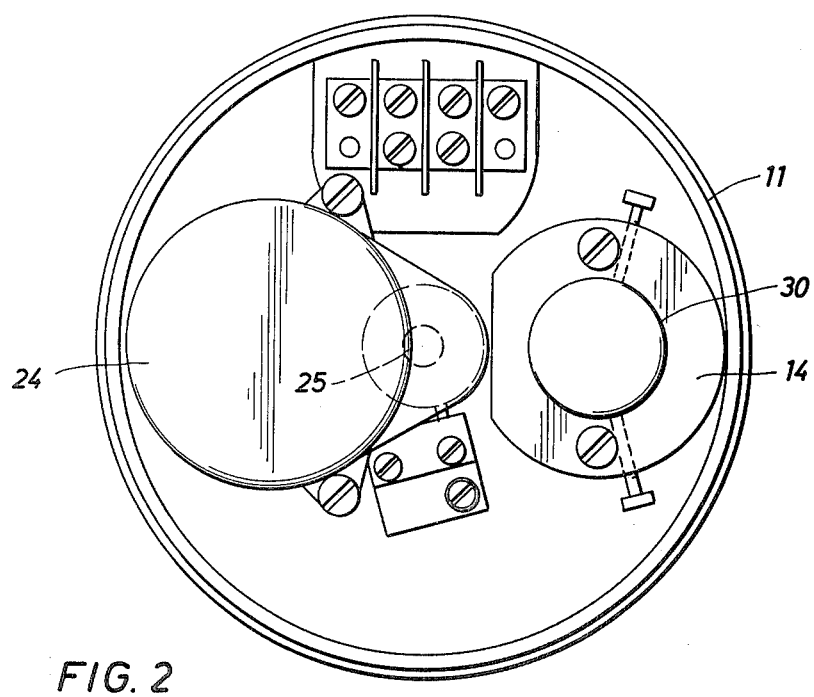
FIG. 2 is a top view of the apparatus shown in FIG. 1.

Referring now to FIGS. 1 and 2, there is shown an apparatus for carrying out the method of this invention having a main frame member 10 for supporting the turntable 13. A circular spacing ring 11 disposed on the main frame member supports a base plate 12 with the turntable 13 being supported on a shaft 25 which extends downwardly through the base plate. The galvanic cell 30 is secured to a cell support member 14 that is fastened to the base plate. The base plate has an opening 15 that aligns with the opening 16 and 17 in the turntable.

The turntable is provided with two diametrically opposite openings 16 and 17 that have an inwardly projecting shoulder for supporting a disc 23 of filter paper. This provides a simple means for supporting the disc of filter paper and permits placement of a sample of the gasoline directly on the filter paper. In addition, since the filter paper is exposed both on the top and the bottom to the atmosphere, the aromatics and olefins will be rapidly evaporated from the sample. The turntable is driven by a geared motor 24 which may be controlled by the circuit shown in FIG. 3. The circuit should provide means for controlling the evaporation time of the sample as well as rotating the turntable a fixed amount and at a controlled rate so that the sample is rotated past the galvanic cell and the turntable returned to a position where a new filter disc and sample may be placed in the sample holder. The shaft 25 which supports the turntable forms a part of the drive means and extends through the top frame of the support. The turntable and galvanic cell support should be constructed so that the gap between the filter paper disc and the sensor electrode of the cell is a minimum without physical contact.

The galvanic cell 30 is substantially the same as the cell shown in the above-referenced patent. The cell comprises an open-top container, preferably a small bottle having a screw top which may be readily threaded into the support 14. The bottle is filled with an electrolyte which is, preferably, a silver tetraflouroborate solution in 90% butyl alcohol and 10% water. A wick means extends into the electrolyte and is used to transport the electrolyte to a filter disc positioned between the counter electrode and the sensing electrode. The electrodes and the filter disc are assembled as a unit and mounted on top of the support member. The detailed construction of the cell is described in the above-referenced patent that is incorporated by reference.

Figure 3:
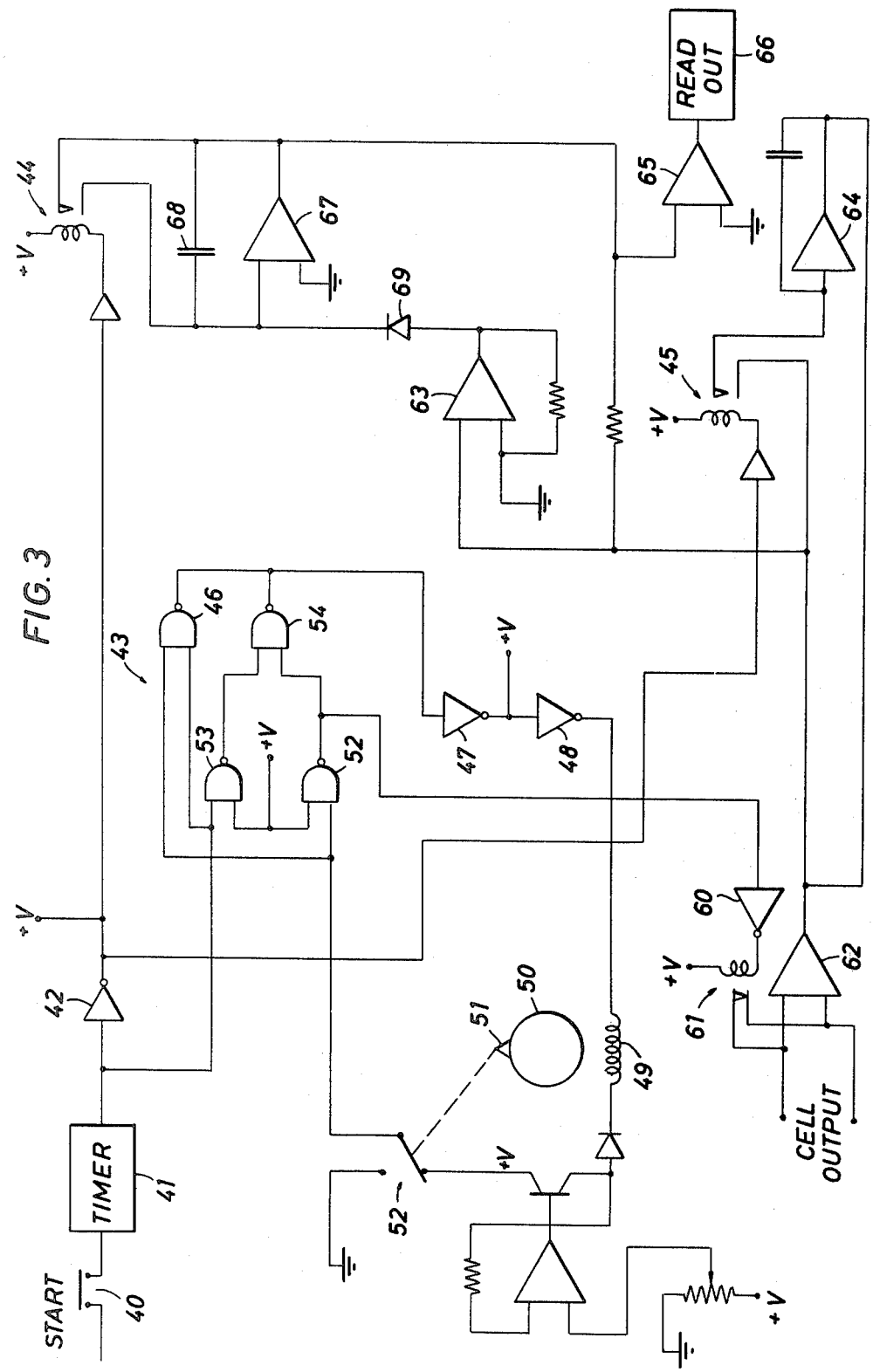
FIG. 3 is a block diagram of the circuit used to control the apparatus.

Referring now FIG. 3 there is shown a block diagram of a circuit for controlling the operation of the instrument. The circuit is provided with a timer 41 having a controllable period and a switch 40 for initiating the start of the cycle. The timer is designed so that when it is started it will provide a high level output which is supplied both to an inverter 42 and the NAND gates 46 and 53 the logic circuit 43. A high level input turns off inverter 42 to provide a low level output which is used to close both the relay 44 and the relay 45. Closing the relay 44 effectively zeros the peak picking amplifier 67 while closing of the relay 45 zeros the instrument amplifier 62.

The NAND gate 46 is coupled to the positive voltage side of the microswitch 52 whose operation is controlled by the lobe 51 on a cam 50 driven by the instrument motor. The microswitch 52 is positioned so that it is normally grounded and is moved to the positive voltage supply by the lobe 51 of the cam. This occurs at the end of a cycle and stops the motor. Thus, at the beginning of a cycle the NAND gate 46 will have a high voltage level at one input from the microswitch and be supplied with a high voltage level at its other input from the timer 41. This will cause its output to go low and activate the inverter 47 to supply high voltage level at its output. The combination of the positive voltage and high voltage level on the inverter 47 will cause the inverter 48 to turn off and supply a low voltage at its output. This will allow the motor coil 49 to be energized from the power supply. As soon as the motor starts the microswitch will move off the lobe 51 and ground the microswitch. This will, of course, supply a low voltage to one input of the NAND gate 46 which will cause the gate to open and supply a high voltage at its output. This high voltage will turn off the inverter 47 and cause its output to go low which will effectively ground the voltage supply and turn on the inverter 48. This will remove the ground from the motor coil 49 and stop the motor. The motor will remain in a stop position until the timer 41 completes its cycle at which time the timer output will go low. The low voltage from the timer output will be supplied to the NAND gate 53 which will cause the gate to supply a high voltage output to the input of the NAND gate 54. The NAND gate 52 is supplied with high voltage power supply and a ground signal from the microswitch 52 and supply a high voltage output. The two high level inputs will close gate 54 and provide a low voltage output. The low voltage output will turn on the inverter 47 which will turn off the inverter 48 causing a low voltage to be applied to the ground lead of the motor coil 49. The high level output from the NAND gate 52 will also turn on the inverter 60 which will energize the relay 61 to open the relay contacts and connect the instrument amplifier 62 to the cell. The motor will continue to rotate the turntable and pass the sample holder over the sensing electrode of the cell. The signal produced by the cell will be amplified by the amplifier 62 and fed to the peak-picking circuit consisting of the amplifiers 63 and 67. The amplifier 63 will continue to feed a signal to the amplifier 67 as long as the signal stored on the feedback capacitor 68 of the amplifier 67 is below the level of the output of the amplifier 63. Once the signal from the amplifier 63 falls below the level of the amplifier 67 the diode 69 will block the feedback of the signal to the amplifier 63. This peak signal will be amplified by amplifier 65 and displayed on a readout 66 which may utilize analog to digital conversion in combination with a light emitting diode display.

As the motor continues to rotate the lobe 51 will again close the microswitch on the positive voltage supply. This will supply high level to both inputs of the NAND gate 52 causing its output to go low which will turn off the inverter 60 and allow the relay 61 to close thus shorting the instrument amplifier 62. The high level output of the microswitch supplies an input to the NAND gate 46 which will cause its output to go high turning on the inverter 47 which in turn will turn off the inverter 48 stopping the motor. The system will remain in this state until the start switch 40 is again depressed at which time the cycle will repeat itself.

From the above brief description it is seen that the circuit supplies the proper commands for determining the time delay during which the sample is allowed to evaporate from the filter disc and then energizes the motor driving the turntable to pass the filter disc over the top of the sensing cell. The time during which the sample is allowed to evaporate is controlled by adjusting the period of timer 41. Also by controlling the voltage level of the amplifier used for supplying power to the motor coil 49, the speed of the motor driving the turntable can be controlled.

Referring now to FIG. 4, there is shown a plot of the response of the instrument to various tetraalkylleads with respect to various evaporation times. Also shown is the actual lead content of the sample as measured by the atomic absorption method. The atomic absorption method is, of course, the standard for measuring the lead content of gasolines and used to authenticate the performance of any other method for measuring the lead content. As seen from the data of FIG. 4, a longer evaporation time for gasoline containing either tetraethyl lead is required to obtain maximum instrument response than in the case of tetramethyl lead or a mixture of leads referred to as MLA-500. It is possible to accurately calibrate the instrument using samples leaving known amounts of leadalkyls so that it reads the lead content of the gasoline sample directly.

The data of FIG. 4 was obtained using the apparatus as shown in FIGS. 1 and 2 described above by placing 50 ul samples on the filter paper disc. After the samples were placed on the disc, the program timer allowed the sample to evaporate for the required time and then moved the turntable so that the sample passed over the top of the galvanic cell. During the passage of the sample over the top of the galvanic cell sufficient of the tetraalkyllead reaches the sensing electrode by evaporation across the thin air gap to produce the required response from the cell. The timing mechanism then returns the turntable to a rest position where a new filter disc can be loaded into the sample holder and another sample of the gasoline placed on the filter disc.

Once the instrument is calibrated for a particular lead alkyl and the times adjusted, relatively unskilled labor can be used to operate the instrument to check the lead content of the various gasoline samples. Also, it is possible to automate the operation of the instrument so that it can be used as a monitoring device in monitoring the lead content of gasolines at various refinery installations. The instrument can also be automated so that will monitor the lead content of gasolines transported in pipelines. This latter operation is extremely important where a load of nonleaded gasoline follows a load of leaded gasoline in a common carrier pipeline. Due to the severe restrictions on the lead content of nonleaded gasoline it is, of course, necessary to completely segregate the two gasolines.

I claim as my invention:

1. An improved galvanic detector for measuring trace amounts of lead in gasoline, said detector comprising:

a frame member, a turntable having at least one sample receiving means disposed on its surface, said turntable being rotatably mounted on said frame member and said sample receiving means comprising an opening formed in the surface of said turntable and adapted to receive and support a porous carrier medium which is capable of absorbing a sample of gasoline;

a galvanic cell, said galvanic cell being mounted on said frame member with its electrodes adjacent the path of said turntable; and, a motor means coupled to said turntable to rotate said turntable so that said sample receiving means passes in close proximity to electrodes of said galvanic cell.

2. The detector of claim 1 wherein the wall of said opening has an inwardly projecting shoulder adapted to support said carrier medium in said opening.

3. The detector of claim 1 wherein said galvanic cell comprises an open top container, a sensing electrode and a counter electrode mounted on said frame member, said container being removably mounted on said frame member adjacent said electrodes, a porous medium being disposed between said electrodes, and communication means for establishing fluid communication between an electrolyte in said container and the porous medium between said electrodes.

4. The detector of claim 1 and in addition circuit means for controlling the motor means used for rotating said turntable.

5. The detector of claim 4 wherein said circuit means has provisions for controlling the time interval said turntable remains at rest prior to said motor means rotating said turntable.

* * * * *